US012609049B1

(12) United States Patent (10) Patent No.: US 12,609,049 B1

McGowan (45) Date of Patent: Apr. 21, 2026

(54) VISUAL SENSOR DEVICE FOR PERFORMING CPR

(71) Applicant: Colleen McGowan, Matawan, NJ (US)

(72) Inventor: Colleen McGowan, Matawan, NJ (US)

(73) Assignee: Colleen McGowan, Matawan, NJ (US)

( * ) Notice: Subject to any disclaimer, the term of this patent is extended or adjusted under 35 U.S.C. 154(b) by 260 days.

(21) Appl. No.: 18/517,761

(22) Filed: Nov. 22, 2023

Related U.S. Application Data

(60) Provisional application No. 63/465,951, filed on May 12, 2023.

(51) Int. Cl.
| | |
|---|---|
| *G09B 23/28* | (2006.01) |
| *A61B 5/00* | (2006.01) |
| *H05B 47/155* | (2020.01) |
| *H05B 47/16* | (2020.01) |

(52) U.S. Cl.
CPC .......... *G09B 23/288* (2013.01); *A61B 5/6833* (2013.01); *A61B 5/68335* (2017.08); *A61B 5/742* (2013.01); *H05B 47/155* (2020.01); *H05B 47/16* (2020.01); *A61B 2560/0285* (2013.01); *A61B 2560/0462* (2013.01)

(58) Field of Classification Search
CPC ....... G09B 23/28; G09B 23/288; G09B 23/30
See application file for complete search history.

(56) References Cited

U.S. PATENT DOCUMENTS

| | | | |
|---|---|---|---|
| 4,491,423 A | 1/1985 | Cohen | |
| 4,797,104 A * | 1/1989 | Laerdal | ................ G09B 23/288 |
| | | | 434/428 |

| | | | |
|---|---|---|---|
| 4,863,385 A * | 9/1989 | Pierce | .................. G09B 23/288 |
| | | | 601/41 |
| 5,036,742 A | 8/1991 | Youakim | |
| 5,214,228 A | 5/1993 | Hoiles et al. | |
| 5,239,988 A | 8/1993 | Swanson et al. | |
| 5,592,143 A | 1/1997 | Romney et al. | |
| 5,944,018 A * | 8/1999 | Allgood | ................. A61H 31/00 |
| | | | 128/897 |
| 6,427,685 B1 * | 8/2002 | Ray | ...................... G09B 23/288 |
| | | | 434/262 |
| D671,649 S * | 11/2012 | McCormack | ................ D24/168 |
| 8,317,519 B1 * | 11/2012 | Orlando | ............... G09B 23/288 |
| | | | 434/262 |

(Continued)

FOREIGN PATENT DOCUMENTS

| | | |
|---|---|---|
| EP | 2266661 B1 | 8/2016 |
| EP | 4043062 A1 | 8/2022 |

*Primary Examiner* — Kurt Fernstrom

(74) *Attorney, Agent, or Firm* — Gearhart Law LLC

(57) ABSTRACT

The present invention is directed to a visual sensor device that is designed and configured to be used by a rescuer on a patient during CPR. The visual sensor device is configured to alert a rescuer on the real-time number of compressions and/or resuscitations required on the patient during CPR. The visual sensor device may include a rectangular housing including a plurality of LEDs, a battery, a timer circuit, and a sensor. The rectangular housing may further include a removable adhesive and be configured to be placed on the body of a patient. The removable adhesive may allow for the device to be easily disposable after a single use, and further, allows for the device to be easily portable and placed on the body of the patient while in use.

20 Claims, 5 Drawing Sheets

(56)         References Cited

U.S. PATENT DOCUMENTS

| | | | |
|---|---|---|---|
| 8,600,522 B2 * | 12/2013 | Peterson .............. | A61H 31/007 |
| | | | 600/509 |
| 9,522,096 B2 * | 12/2016 | Jensen ................... | A61N 1/046 |
| 10,182,966 B2 | 1/2019 | Freeman et al. | |
| 10,204,389 B2 * | 2/2019 | Packer ................... | G16H 10/60 |
| 11,202,579 B2 * | 12/2021 | Freeman ............. | G09B 23/288 |
| 11,819,369 B2 * | 11/2023 | Freeman .................. | A61B 1/05 |
| 2008/0176199 A1 * | 7/2008 | Stickney .............. | A61B 5/0535 |
| | | | 600/509 |
| 2010/0022904 A1 * | 1/2010 | Centen ................ | A61N 1/3925 |
| | | | 600/595 |
| 2017/0135171 A1 | 5/2017 | Jung et al. | |
| 2017/0252525 A1 * | 9/2017 | Fournier .......... | A61M 16/0051 |
| 2018/0147378 A1 * | 5/2018 | Jacquot ............... | A61M 16/205 |
| 2022/0304890 A1 * | 9/2022 | Kohler ................ | A61H 31/007 |
| 2023/0186788 A1 * | 6/2023 | Charlton .................. | G09B 5/02 |
| | | | 434/265 |
| 2024/0423869 A1 * | 12/2024 | Kleinman ............ | A61H 31/006 |

* cited by examiner

VISUAL SENSOR DEVICE FOR PERFORMING CPR

FIELD OF THE INVENTION

The present invention pertains to the field of medical devices, specifically to a visual sensor device designed for use during cardiopulmonary resuscitation (CPR). This invention falls under the category of emergency medical equipment, with a focus on improving the effectiveness and efficiency of CPR performed by rescuers in various settings.

BACKGROUND OF THE INVENTION

Cardiopulmonary resuscitation (CPR) is an essential emergency procedure used in critical situations such as cardiac arrest, where the heart stops beating or beats ineffectively. The main objective of CPR is to restore partial flow of oxygenated blood to the brain and heart, extending the window for successful resuscitation without permanent brain damage. This life-saving technique involves chest compressions combined with artificial ventilation, either by mouth-to-mouth resuscitation or with the aid of a device providing positive pressure ventilation. The effectiveness of CPR significantly influences the survival rate and long-term outcome in cases of cardiac arrest, making the proficiency in its application crucial.

The American Heart Association (AHA) provides specific guidelines for performing CPR, which vary based on the age of the patient. For adults, the AHA recommends a rate of 100 to 120 chest compressions per minute, with each compression being at least two inches deep and allowing the chest to completely recoil between compressions. In addition to chest compressions, it is advised to provide two resuscitative breaths after every 30 compressions. In the case of infants and pediatric patients, the guideline remains 100 to 120 compressions per minute, but the depth of compressions differs: about 1.5 inches for infants and about 2 inches for children. The ratio of compressions to breaths in a one-rescuer scenario is 30 compressions followed by two breaths, similar to adults. However, in a two-rescuer scenario for infants and children, the ratio changes to 15 compressions followed by two breaths, acknowledging the higher oxygen demand in these younger patients.

Despite the widespread training in CPR techniques, the actual application in real-life scenarios often falls short of these recommended standards, leading to lower survival rates. Factors such as stress, panic, physical fatigue, and the lack of real-time feedback can significantly impair the quality of CPR administered. This discrepancy between training and real-life application highlights a critical gap in the current approach to CPR.

In response to this issue, various CPR assistance devices have been developed, ranging from simple metronomes to sophisticated machines that provide auditory or visual cues to guide the compression rate. However, these devices have several limitations. One major drawback is their lack of adaptability to different patient groups. The optimal technique for performing CPR on adults differs significantly from that for children or infants, and most existing devices do not account for these variations, leading to a one-size-fits-all approach that may not be ideal in all situations.

Another limitation of current CPR assistance devices is their complexity and cost. Some of the more sophisticated devices are expensive and require significant training to use effectively. This restricts their availability, particularly in public places or resource-limited settings where they might be most needed. Furthermore, in high-stress scenarios such as a cardiac arrest, even healthcare professionals may find it challenging to operate complex devices efficiently. The need for a device that is intuitive and easy to use, regardless of the user's level of training, is therefore evident.

Additionally, the issue of skill retention poses a significant challenge in the field of CPR. Studies have shown that the proficiency in CPR techniques declines over time if not regularly practiced. This decay in skills can lead to ineffective CPR when it is most needed. Current training methods and devices do not adequately address this issue, emphasizing the need for a solution that not only assists during CPR but also helps maintain and refresh the skills of potential rescuers.

The primary problem, therefore, is the absence of a simple, intuitive, and adaptive device that can provide real-time, patient-specific feedback during CPR. Such a device should ideally be accessible and easy to use for individuals with varying levels of training, including untrained bystanders, and adaptable to different patient needs. The device should guide the rescuer in maintaining the correct rate of compressions, and assist with the timing of ventilations, all while being cost-effective and easy to deploy in various emergency situations.

The importance of effective CPR cannot be overstated, as it is often the critical factor determining the survival and long-term outcome of individuals experiencing cardiac arrest. The development of new technologies and devices in this field is thus of paramount importance. An ideal solution would bridge the gap between training and real-life application, ensuring that high-quality CPR is delivered consistently, irrespective of the rescuer's background or the patient's specific characteristics. This need for innovation in the field of emergency medical equipment underscores the significance of advancements that can be widely disseminated and utilized in a range of environments, from healthcare settings to public spaces.

SUMMARY OF THE INVENTION

The present invention relates to a visual sensor device designed for use in cardiopulmonary resuscitation (CPR). This device is configured to provide real-time guidance on the number of compressions and resuscitations required during CPR. It may comprise a rectangular housing containing a plurality of LEDs, a battery, a timer circuit, and a sensor. The housing includes a removable adhesive, allowing it to be placed directly on the patient's body. The sensor is triggered upon removal of the adhesive, facilitating immediate operational readiness. Additionally, the device features a timer circuit in electronic communication with the LEDs, which can be adjusted based on the patient's age. This invention also encompasses a method for using the visual sensor device in CPR scenarios.

The visual sensor device introduced in this invention offers numerous advantages over existing CPR assistance technologies. A key feature is its real-time feedback mechanism, which aids rescuers in maintaining the appropriate rate of compressions and respirations, a critical factor in effective CPR. Distinct from many existing devices, this invention is uniquely adaptable to varying patient age groups, thus enhancing its utility across different demographics. One notable innovation is the incorporation of separate lights for each action (compression and resuscitation), providing clear, distinct visual cues for each required action. This feature simplifies the CPR process, allowing for more accurate and timely responses, particularly important in high-stress emergency scenarios.

The device's intuitive design, characterized by a simple activation mechanism through the removal of adhesive and immediate visual feedback from LEDs, ensures ease of use, even for those under extreme pressure. Its portable and user-friendly nature broadens its applicability, making it an essential tool not only for professional healthcare providers but also for untrained bystanders. By effectively bridging the gap between CPR training and real-world application, the invention significantly improves the quality of emergency care provided during cardiac arrest situations, enhancing the chances of successful resuscitation and patient survival.

In a first implementation of the invention, a visual sensor device for performing CPR comprises:

a housing having an interior portion and exterior portion, the housing including:

a timer circuit;

a plurality of LED lights in electronic communication with the timer circuit, the plurality of LED lights extending to the exterior portion;

a sensor in electronic communication with the timer circuit; and a battery in electronic communication with the timer circuit and the sensor; wherein the sensor is triggered by a removable release paper on the exterior portion of the housing.

In a second aspect, the housing may be comprised of a paper-based product.

In another aspect, the housing may be rectangular in shape.

In another aspect, the interior portion of the housing may fully include the timer circuit, the battery, and the sensor.

In another aspect, the interior portion may further include a portion of the plurality of LEDs, wherein another portion of the LEDs extends to the exterior portion of the housing.

In another aspect, the plurality of LED lights may include a first LED light and a second LED light.

In another aspect, the timer circuit may be configured to provide the number of blinks per minute for a first LED light, wherein the number of blinks represents the number of chest compressions per minute.

In another aspect, the timer circuit may be configured to have the second LED light blink, wherein the blinking of the second LED light represents the period of time during CPR the rescuer provides resuscitative breaths to the patient.

In another aspect, the second LED light may be turned on at the same time or at a different time than the first LED light.

In another aspect, the first LED light may be a first color.

In another aspect, the second LED light may be a second color.

In another aspect, the release paper may be a tab on the exterior portion of the housing.

In another aspect, the release paper may expose an adhesive on a bottom side of the exterior portion of the housing.

In another aspect, the adhesive may be adapted to fit on the body of a patient.

In another aspect, the device may be configured to be portable.

In another aspect, the device may be configured to be disposable.

In a second implementation of the invention, a method of using a visual sensor device for performing CPR comprises:

obtaining a visual sensor device for performing CPR, the visual sensor device having a housing with an interior portion and exterior portion, the housing including a timer circuit, a plurality of LED lights in electronic communication with the timer circuit, the plurality of LED lights extending to the exterior portion, a sensor in electronic communication with the timer circuit, and a battery in electronic communication with the timer circuit and the sensor, wherein the sensor is triggered by a removable release paper on the exterior portion of the housing;

removing the removable release paper such that an adhesive portion is showing and placing the adhesive portion on a body part of a patient;

having the sensor trigger the timer circuit to start the plurality of LEDs upon removing the removable release paper;

providing chest compressions to the patient at the rate given by a blink on a first LED light of the plurality of LED lights; and providing resuscitative breaths to a patient upon a blinking of a second LED light of the plurality of LED lights.

In another aspect, the timer circuit may be configured to provide the number of blinks per minute for the first LED light, wherein the number of blinks represents the number of chest compressions per minute.

In another aspect, the first LED light may blink at a rate of 100-120 blinks per minute.

In another aspect, the timer circuit may be configured to have the second LED light blink, wherein the blinking of the second LED light represents the period of time during CPR the rescuer provides breaths to the patient.

In another aspect, the second LED light may blink every 30 chest compressions per CPR guidelines In another aspect, the first LED light and second LED light exhibit different colors.

In a third implementation of the invention, the visual sensor device for performing CPR accommodates a two-man rescue operation by including an additional set of LED indicators configured to synchronize with a two-rescuer CPR protocol. The device comprises:

a housing having an interior portion and exterior portion, the housing including a timer circuit, a sensor, and a battery all in electronic communication with each other;

a plurality of LED lights in electronic communication with the timer circuit, extending to the exterior portion, wherein the plurality of LED lights includes a first set of LED lights and a second set of LED lights;

a removable release paper on the exterior portion of the housing that triggers the sensor when removed;

wherein the timer circuit is further configured to alternate the blinking of the first set of LED lights and the second set of LED lights to indicate the switch between compression provider and breath provider in a two-man CPR scenario;

wherein the first set of LED lights is configured to blink at a rate of 100-120 blinks per minute to guide the rescuer responsible for chest compressions;

wherein the second set of LED lights is configured to blink at prescribed intervals to indicate to the second rescuer when to provide resuscitative breaths, at a rate of two breaths every 15 compressions as per two-man CPR guidelines for children and infants.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 6 presents a flowchart of a method of use of the visual sensor device for performing CPR illustrated in FIG. 1;

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward visual sensor device for performing CPR that is designed and configured to be placed on the body of a patient suffering from cardiac arrest such that a rescuer may be visually aware of the rate that chest compressions need to be provided, as well as the period of time at which breaths are to be provided to the patient. The visual sensor device may include a housing having and interior portion and an exterior portion. The interior portion of the housing may contain the majority of the components of the sensor device, including a timer circuit, a sensor, and battery. The exterior portion of the housing may include a plurality of visual aids, such as a plurality of LED lights, as well as an adhesive. The visual sensor device operates by allowing a rescuer to use visual cues from the device to provide both chest compressions, as well as breaths to the patient during CPR at the desired rate as recommend by health guidelines. Additionally, the device is configured to start once the adhesive is removed and allows for a rescuer to easily place the device on a body part of the patient.

Figure 1A:
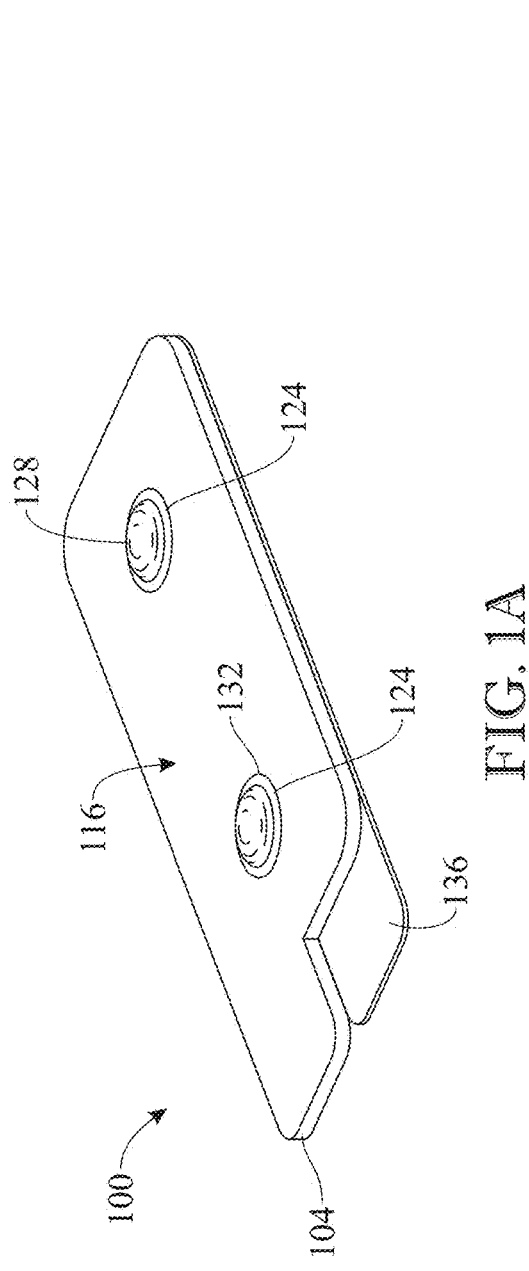
FIG. 1A presents a top isometric view of a visual sensor device for performing CPR, shown in accordance with a first illustrative embodiment of the invention.
Figure 1B:
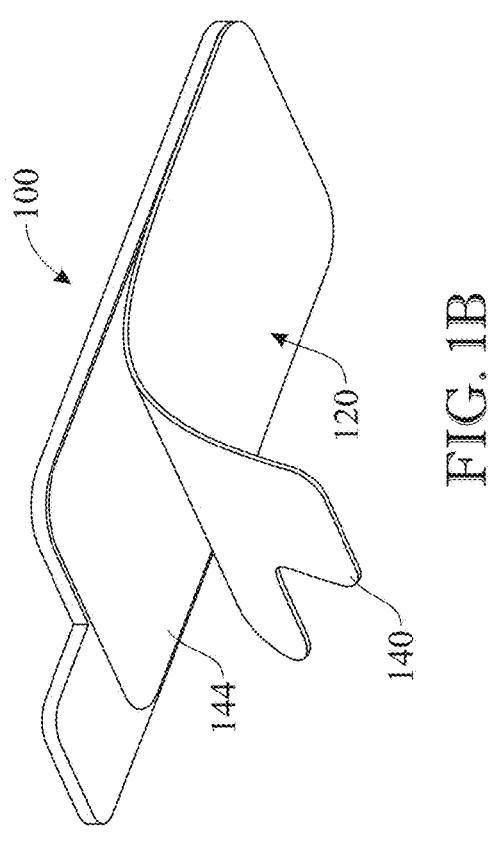
FIG. 1B presents a bottom isometric view of the visual sensor device for performing CPR illustrated in FIG. 1A, shown with a removable adhesive tab partially removed.
Figure 3:
FIG. 3 presents a top perspective view of the visual sensor device for performing CPR illustrated in FIG. 1A, shown with the internal components of the device within the housing of the device.

Referring initially to FIG. 3, a visual sensor device for performing CPR 100 is illustrated in accordance with an exemplary embodiment of the present invention. As shown, the sensor device 100 includes a housing 104 having an interior portion 108 and an exterior portion 112. The housing 104 may be comprised of a paper-based product and in the preferred embodiment, may be rectangular in shape. Embodiments are envisioned wherein the housing 104 may conform to any shape capable of housing all the requisite components. Referring now to FIGS. 1A and 1B, the exterior portion of the housing 104 may include a top side 116 and a bottom side 120. The top side 116 may include a plurality of LEDs 124. In the preferred embodiment the plurality of LEDs may include a first LED 128 and a second LED 132. Additionally, the top side 116 may include a depressed region having a tab 136.

With continued reference to FIG. 1B, the tab 136 may define a removable release paper 140 on the bottom side 120 of the exterior portion 112 of the housing 104. The removal of the release paper 140 may expose an adhesive 144 on the bottom side 120 of the exterior portion 112 of the housing 104, wherein the adhesive 144 is configured to adhere to a body part of a patient.

Figure 4:
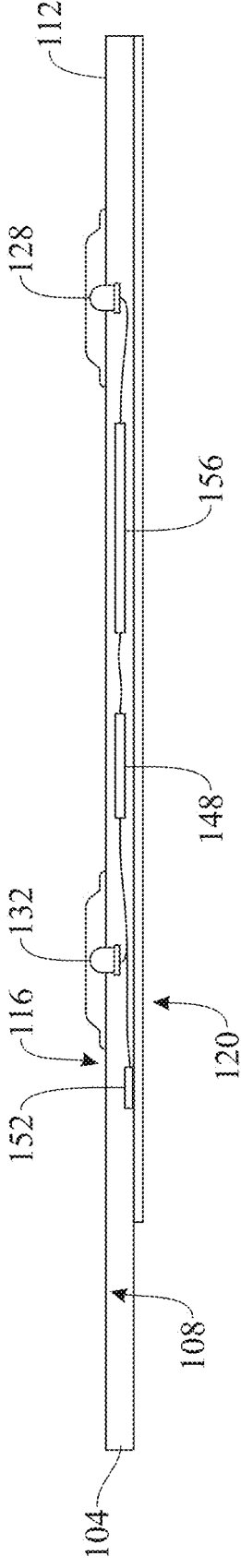
FIG. 4 presents a side view of the visual sensor device for performing CPR illustrated in FIG. 3, shown with the internal components of the device within the housing of the device.

Referring back to FIG. 3, and also shown in FIG. 4, the housing 104 may include a number of interior components within the interior portion 108. These interior components may include a timer circuit 148, the aforementioned plurality of LEDs 124, a sensor 152, and a battery 156. The plurality of LEDs 124 may be in electronic communication with the timer circuit 148, wherein the plurality of LED lights extend from the interior portion 108 to the exterior portion 112. More particularly, the timer circuit 148 may be configured to provide the number of blinks per minute for the first LED light 128, wherein the number of blinks represents the number of chest compressions per minute. The timer circuit 148 may also be configured to have the second LED light blink 132, wherein the blinking of the second LED light represents the period of time during CPR the rescuer provides breaths to the patient. The second LED light 132 may be turned on at the same time or at a different time than the first LED light 128. In the preferred embodiment, the first LED 128 and the second LED 132 may each be different colors.

With continued reference to FIG. 3, the battery 156 may be in electronic communication with the timer circuit 148 and the sensor 152, providing power to each. Additionally, the sensor 152 may be triggered by the removable release paper 140 on the exterior portion 112 of the housing 104.

The sensor 152 may then start the timer circuit 148 such that a rescuer may begin administer CPR.

Figure 5:
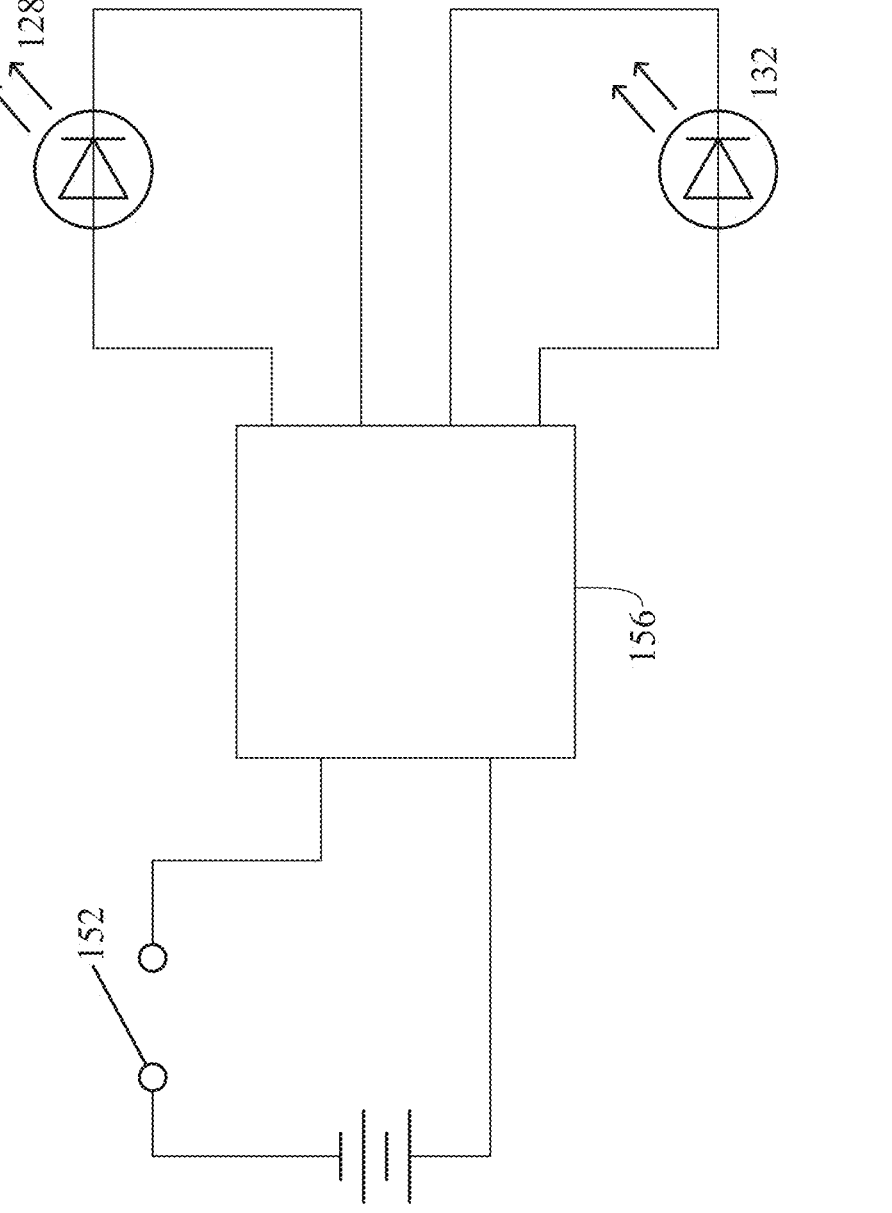
FIG. 5 presents a sample circuit of the internal components within the housing visual sensor device for performing CPR illustrated in FIG. 3.

The timer circuit 148 is shown in FIG. 5. As shown, the sensor 152 opens the circuit and sets off the first LED and the second LED at a set time interval. For instance, the first LED light blinks may at a rate of 100-120 blinks per minute, wherein the number of blinks represents the number of chest compressions per minute. Similarly, the second LED light may blink every 30 seconds, wherein the blinking of the second LED light represents the period of time during CPR the rescuer provides breaths to the patient.

The illustrations of FIGS. 1-3 and FIG. 6 demonstrates an example method of operation of the visual sensor device for performing CPR 100 when a patient 164 may be experiencing cardiac arrest. The first step may involve having a rescuer 160 remove the removable release paper 140 by pulling on tab 136. Removing the release paper 140 allows for the adhesive 144 to be exposed. Upon exposing the adhesive 144, the device 100 may be placed on a body part of the patient 164. As shown, the device 100 is placed on the chest of the patient 166.

Figure 2:
FIG. 2 presents a perspective view of the visual sensor device for performing CPR illustrated in FIG. 1A and FIG. 1B, shown prior to adhering the device to a patient's skin and visible to the rescuer performing CPR.

The next step involves having the sensor 152 trigger the timer circuit 148 to start the plurality of LEDs 124 upon removing the removable release paper 140. The timer circuit 148 may be configured to provide the number of blinks per minute for the first LED light 128, wherein the number of blinks represents the number of chest compressions per minute. While the first LED light blinks, the rescuer 160 may provide chest compressions 168, as best shown in FIG. 2, to the patient 164 at the rate given by a blink on a first LED light 128 of the plurality of LED lights 128. The first LED light may blink at a rate of 100-120 blinks per minute. Upon providing chest compressions, the next step 300 may be having the rescuer 160 provide breaths to a patient upon a blinking of a second LED light 132 of the plurality of LED lights 124. The second LED light may blink every 30 seconds.

Alternative embodiments are contemplated to those shown or described herein without departing from the scope of the present disclosure. For example, embodiments are contemplated in which the timing of the LED lights through the timer circuit may vary, such as if the patient is a child the timer circuit may be timed to provide chest compressions and breaths at a different rate. Additionally, embodiments are considered wherein the material of the housing of the device is made of a durable material such that the device may be able to reused multiple times. Along those lines, the adhesive may also be replaced with a reusable material.

In some embodiments, the timer circuit 148 may include an adjustment feature that allows the device to be calibrated based on the patient's age. This adjustability ensures that the device provides accurate and effective guidance for CPR regardless of whether the patient is an adult, child, or infant. For pediatric/infant patients, the device may alter the blinking sequence of the LEDs to indicate a higher frequency of breaths, in line with pediatric/infant CPR guidelines which suggest a different compression to breath ratio, particularly in a two-rescuer scenario.

The battery 156 used within the device is chosen for its long-life capabilities, ensuring that it can power the visual sensor device for the duration of CPR, which may be extended in some emergency situations. The long-life battery mitigates the risk of the device failing due to power depletion during critical resuscitation efforts. Moreover, the battery may be user-replaceable, allowing the device to be prepared swiftly for reuse if necessary.

Further to the plurality of LED lights, the visual sensor device may incorporate a third LED light dedicated to indicating the operational status of the device. This LED could emit a distinct color or blink in a specific pattern to signal that the device is powered and functioning correctly. This feature provides immediate feedback to the rescuer, confirming that the visual cues for CPR are active and reliable.

In another embodiment, the visual sensor device may feature a user interface integrated into the housing 104. This interface can include buttons or touch-sensitive areas that allow the rescuer to configure the timer circuit 148 before initiating CPR. Through this interface, the rescuer could set the device for different CPR protocols, adjust the rates of the LED lights, or even pause and resume the visual cues as needed during the resuscitation process.

The housing 104 may also be enhanced with a waterproof coating or constructed from waterproof materials. This ensures that the device's components are protected from fluids, which are often present in emergency situations. The waterproofing feature enhances the durability of the device and ensures it functions correctly even when exposed to such conditions.

In summary, the visual sensor device for performing CPR disclosed herein provides a more efficient and safer method of conducting CPR by providing visual cues to the rescuer with respect to the appropriate chest compression rate. Also, the device helps alert the rescuer for the appropriate time to provide breaths to the patient. The device is easily portable and disposable after each use, however embodiments are envisioned where the device may be used multiple times before disposal.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A visual sensor device for performing CPR, the device comprising:
   a housing having an interior portion and am exterior portion, the housing including: a timer circuit within the interior portion;
   a plurality of LED lights in electronic communication with the timer circuit, the plurality of LED lights extending to the exterior portion;
   a sensor within the interior portion in electronic communication with the timer circuit;
   and
   a battery within the interior portion in electronic communication with the timer circuit and the sensor; wherein the sensor is triggered by removing a release paper covering a removable adhesive on the exterior portion of the housing.

2. The device of claim 1, wherein the housing is rectangular in shape.

3. The device of claim 1, wherein the housing is comprised of a paper-based product.

4. The device of claim 1, wherein the plurality of LED lights includes a first LED light and a second LED light.

5. The device of claim 4, wherein the first LED light is configured to blink at a rate corresponding to the recommended number of chest compressions per minute.

6. The device of claim 4, wherein the second LED light is configured to indicate the timing for providing resuscitative breaths to the patient.

7. The device of claim 6, wherein the second LED light blinks in a pattern distinct from the blinking of the first LED light.

8. The device of claim 4, wherein the first LED light is a first color, and the second LED light is a second color.

9. The device of claim 1, wherein the removable adhesive is covered by the release paper configured as a tab.

10. The device of claim 9, wherein the release paper, when removed, exposes an adhesive capable of securing the device to a patient's body.

11. The device of claim 1, wherein the adhesive is hypoallergenic and suitable for maintaining adhesion to the patient's skin during CPR.

12. The device of claim 1, wherein the sensor is configured to be activated upon the removal of the adhesive and the placement of the device on the patient's body.

13. The device of claim 1, wherein the timer circuit is adjustable based on the age of the patient.

14. The device of claim 1, wherein the battery is a long-life battery designed to last the duration of the expected CPR procedure.

15. The device of claim 1, wherein the plurality of LED lights further includes a third LED light for indicating the activation status of the device.

16. The device of claim 1, wherein the device further comprises a user interface for configuring the timer circuit.

17. The device of claim 16, wherein the user interface includes buttons for adjusting the rate of the first and second LED lights.

18. The device of claim 1, wherein the housing further includes a waterproof coating.

19. A visual sensor device for performing CPR, the device comprising:

a waterproof housing having an interior portion and exterior portion, the housing including:

a timer circuit within the interior portion;

a plurality of LED lights in electronic communication with the timer circuit, the plurality of LED lights extending to the exterior portion, wherein a first LED light is configured to blink at a rate corresponding to the recommended number of chest compressions per minute and a second LED light is configured to indicate the timing for providing resuscitative breaths to the patient;

a sensor within the interior portion in electronic communication with the timer circuit;

and a battery within the interior portion in electronic communication with the timer circuit and the sensor; wherein the sensor is triggered by removing a release paper covering a removable adhesive on the exterior portion of the housing.

20. A visual sensor device for performing CPR, the device comprising:

a waterproof housing having an interior portion and an exterior portion, wherein the housing is rectangular and comprised of a paper-based product, and further wherein the housing includes a user interface;

a timer circuit within the interior portion, the timer circuit being adjustable based on the patient's age and configured to control a plurality of LED lights;

a first LED light and a second LED light among the plurality of LED lights, wherein the first LED light is of a first color configured to blink at a rate of 100-120 blinks per minute to indicate the number of chest compressions per minute, and the second LED light is of a second color configured to blink in synchronization with the first LED light or remain illuminated to indicate the period for providing resuscitative breaths during CPR, and wherein the first and second LED lights are in electronic communication with the timer circuit and extend to the exterior portion of the housing;

a sensor within the interior portion in electronic communication with the timer circuit, wherein the sensor is triggered by the removal of a release paper covering a removable adhesive on the exterior portion of the housing, the adhesive being hypoallergenic and suitable for maintaining adhesion to the patient's skin during CPR;

a battery within the interior portion in electronic communication with the timer circuit, the sensor, and the LED lights, wherein the battery is a long-life battery designed to last the duration of the expected CPR procedure;

wherein the user interface includes buttons for adjusting the rate of the first and second LED lights and for setting the timer circuit according to the specific CPR protocol required for the patient;

wherein the device is portable and disposable, designed to facilitate a single use during an emergency CPR situation.

\* \* \* \* \*